United States Patent [19]

Stavinoha, Jr. et al.

[11] Patent Number: 5,362,890

[45] Date of Patent: Nov. 8, 1994

[54] GAS PHASE PROCESS FOR THE EPOXIDATION OF NON-ALLYLIC OLEFINS

[75] Inventors: Jerome L. Stavinoha, Jr., Longview, Tex.; John R. Monnier, Kingsport, Tenn.; David M. Hitch, Kingsport, Tenn.; Timothy R. Nolen, Kingsport, Tenn.; George L. Oltean, Rochester, N.Y.

[73] Assignee: Eastman Chemical Company, Kingsport, Tenn.

[21] Appl. No.: 130,930

[22] Filed: Oct. 4, 1993

[51] Int. Cl.$^5$ .................. C07D 301/10; C07D 303/04
[52] U.S. Cl. ..................................... 549/536; 549/534; 549/537
[58] Field of Search ............... 549/537, 536, 534

[56] References Cited

U.S. PATENT DOCUMENTS

| | | | |
|---|---|---|---|
| 4,409,394 | 10/1983 | Vangermain et al. | 549/537 |
| 5,057,481 | 10/1991 | Bhasin | 502/208 |
| 5,117,012 | 5/1992 | Stavinoha, Jr. et al. | 549/538 |

FOREIGN PATENT DOCUMENTS

| | | |
|---|---|---|
| 0480537 | 4/1992 | European Pat. Off. . |
| 1382099 | 1/1975 | United Kingdom . |

OTHER PUBLICATIONS

Derwent Abstract WPI Acc. No. 91-245819/34 (Canadian Patent 1,286,687).

*Primary Examiner*—Joseph E. Evans
*Attorney, Agent, or Firm*—J. Frederick Thomsen; Harry G. Gwinnell

[57] ABSTRACT

Disclosed herein is an improved gas phase process for the selective epoxidation of non-allylic olefins wherein the epoxidation is carried out in the presence of certain inert, paraffin hydrocarbons. Such hydrocarbons possess higher heat capacities as compared to other materials, e.g., nitrogen, argon, methane and helium, typically used as inert diluents in olefin epoxidations. The disclosed process is particularly useful for the continuous manufacture of 3,4-epoxy-1-butene from 1,3-butadiene.

6 Claims, No Drawings

GAS PHASE PROCESS FOR THE EPOXIDATION OF NON-ALLYLIC OLEFINS

This invention pertains to an improved gas phase process for the selective epoxidation of non-allylic olefins wherein the epoxidation is carried out in the presence of certain inert, paraffin hydrocarbons. The hydrocarbons useful in the present invention possess higher heat capacities as compared to other materials, e.g., nitrogen, argon, methane and helium, typically used as inert diluents in olefin epoxidations.

Processes for the selective epoxidation of olefins which contain no allylic hydrogen atoms (non-allylic olefins) or olefins which contain hindered allylic hydrogen atoms are described by Monnier and Muehlbauer in U.S. Pat. Nos. 4,897,498, 4,950,773, 5,081,096, 5,138,077 and 5,145,968. Stavinoha and Tolleson disclose in U.S. Pat. No. 5,117,012 the selective epoxidation of 1,3-butadiene to 3,4-epoxy-l-butene (EpB) by contacting a mixture comprising 1,3-butadiene, oxygen and methane with a supported silver catalyst at elevated temperatures.

The state of the art of using diluents in olefin epoxidation is described in Canadian Patents 1,286,687 and 2,053,404 and U.S. Pat. No. 5,057,481 which are limited to ethylene epoxidation. According to these patents, a typical molar compositions of feed gases used in such epoxidation processes are 30 mole percent ethylene, up to 7 mole percent carbon dioxide, up to 5 mole percent ethane with the balance being composed of another inert diluent such as nitrogen or methane. Carbon dioxide is identified as one of the preferred diluent gases for increasing the thermal capacity or heat transfer characteristics of the process gas. According to Canadian Patent 1,286,687, other diluents that function as heat sinks include nitrogen, helium, argon, and lower paraffins such as methane and ethane. However, U.S. Pat. No. 5,057,481 discloses that the use of ethane at concentrations greater than about 5 mole percent results in reduced selectivity in the epoxidation of ethylene to ethylene oxide and lower thermal stability because the chloride concentration on the catalyst surface is lowered. Typical silver catalysts employed in the epoxidation of ethylene contain about 1 to 300 parts by million by weight (ppmw) of Cl on the catalyst surface, both to increase selectivity to ethylene oxide by lowering combustion of ethylene and ethylene oxide to carbon dioxide and water as well as to increase the thermal stability of the silver catalyst. If the level of Cl on the surface of the silver catalyst becomes too low, the reaction becomes excessively exothermic with accompanying loss of selectivity. Ethane acts as a chloride stripping agent and at concentrations above 5 mole percent and at temperatures typically employed in the epoxidation of ethylene, e.g., 230° to 280° C., the degree of chloride stripping becomes unacceptably excessive. As is disclosed in the above-cited patents, one of the problems associated with the use of carbon dioxide as a heat transfer agent (heat sink) in ethylene epoxidation processes is that at levels greater than about 7 mole percent carbon dioxide becomes a reaction inhibitor for ethylene oxide formation. Thus, the concentration of carbon dioxide in feed gas in ethylene epoxidation processes must be limited to concentrations of less than about 7 mole percent. The primary benefit in the use of methane as a diluent is that it permits an increase in the concentration of oxygen which safely may be present in the epoxidation feed gas.

We have discovered that C-2 to C-6 paraffin hydrocarbons may be employed advantageously as inert diluents in the feed gas in the epoxidation of certain olefins. The use of such hydrocarbons permits a substantial increase in the concentration of oxygen which safely may be present in the process feed gas as compared to permissible, maximum, oxygen concentrations when using other diluents, e.g., nitrogen, argon, methane and even helium, normally used in epoxidation processes. For example, when using nitrogen as the inert diluent gas, the maximum oxygen concentration is about 9 mole percent, i.e., higher oxygen concentrations renders the gas mixture explosive. The use of butane as the inert diluent in accordance with the present invention permits oxygen concentrations of up to about 30 mole percent to be used safely. In contrast, the upper limit on oxygen concentration when using methane is about 18 mole percent.

The C-2 to C-6 paraffin hydrocarbons employed in accordance with our invention also possess greater heat capacities than the commonly-used diluents referred to above. The higher heat capacity of the process gas permits the gas to remove a larger amount of the heat generated by the exothermic epoxidation reaction, thereby enabling the epoxidation catalyst bed to be maintained at a lower temperature for a given production rate. This represents a significant advantage for commercial operations since a lower maximum reaction temperature allows operation of the reactor under safer conditions, extends the useful lifetime of the catalyst, and suppresses unwanted, thermal side reactions of the olefin reactant and oxygen. Furthermore, when using a diluent such as n-butane, a higher production rate of desired epoxide may be realized at the same reaction temperature or same temperature rise than may be attained with diluents having lower heat capacities. The use of process diluents having higher heat capacities also is advantageous relative to the design of the commercial reactor.

As is known to those skilled in the art, tubular reactors containing fixed beds of catalyst are the design of choice for vapor-phase, heterogeneous reaction systems. These reactors are operated in a wall-cooled configuration so that heat can be removed continuously, thereby approximating isothermality with the reactor. Isothermal or near-isothermal operation is preferred because the reaction conditions can be maintained within the sometimes narrow optimal temperature range. Operation of the reactor below optimal temperatures usually results in undesirably low reaction/production rates whereas operation above the optimal temperature range can cause poor selectivity and diminished operability due to thermal excursions or runaways. If the combination of diluent heat capacity and radial (through the wall) heat removal capability is insufficient to balance the heat of reaction, thermal runaways are likely to occur and a wall-cooled rector design becomes impractical. Therefore, an important advantage in using a higher heat capacity diluent is the additional heat removal it provides to a wall-cooled reactor which in turn permits near-isothermal operation to be achieved and the optimal commercial reactor design to be employed. Since the heat of reaction is more efficiently transferred from the surface of the catalyst to the walls of the reactor, higher production rates may be realized for a given temperature when higher heat capacity hydrocarbon diluents according to the present invention are used in place of typically used diluent gases. The present invention enables production rates to be increased by up to 50% or higher compared to the use of conventional diluents such as methane when total reaction temperature increases (total ΔT) are kept constant.

Our invention pertains to a continuous process for the preparation of the monoepoxide of an olefin reactant selected from norbornene, norbornadiene and olefins having the general formula

   (I)

wherein $R^1$ is hydrogen or alkyl and $R^2$ is an aryl radical or the group

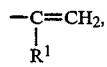

provided that the olefins of formula (I) do not contain any allylic hydrogen atoms, which comprises the steps of:

(1) continuously feeding a gas comprising about 3 to 30 mole percent of said olefin reactant, about 3 to 30 mole percent oxygen and about 40 to 90 mole percent of a paraffin hydrocarbon containing 2 to 6 carbon atoms wherein the oxygen:paraffin hydrocarbon mole ratio is in the range of about 0.03:1 to 0.75:1 to an epoxidation zone containing a supported silver epoxidation catalyst and maintained at a temperature of about 175° to 230° C.; and (2) continuously removing from the epoxidation zone a gas comprising about 0.5 to 3.5 mole percent of said monoepoxide of the olefin reactant, about 2 to 28 mole percent of said olefin reactant, about 2 to 28 mole percent oxygen and about 40 to 90 mole percent of said paraffin hydrocarbon.

Since the olefin reactants employed in our novel process may be catalytically epoxidized at temperatures in the range of about 175° to 230° C. the problem of chloride stripping discussed above is not critical in the practice of our invention.

The supported silver epoxidation catalysts which may be used in the process provided by our invention are known materials which may be prepared according to published procedures including the catalyst manufacturing procedures described in U.S. Pat. Nos. 4,039,561, 4,169,009, 4,267,073, 4,389,338, 4,769,358 and 5,081,096. Thus, the catalysts useful in the present process comprise a catalyst support material having deposited on its surface about 1 to 30 weight percent silver and about 10 to 5000 parts per million by weight (ppmw) of an epoxidation catalyst modifier selected from alkali earth metals, alkaline earth metals and thallium. The weight percentage silver and ppmw modifier (also referred to as promoter) are based on the total weight of the catalyst, i.e., the finished catalyst. Although the modifier component of the catalyst may exist as a salt, oxide or hydroxide of the modifier element, the modifier concentration of the catalyst is based on modifier element alone.

The support component of the catalysts may be selected from the large number of conventional, porous, refractory catalyst carriers or support materials which are essentially inert in the presence of the ethylenically unsaturated compound and oxygen-containing gas feeds and the products in the processes in which the catalysts are employed. Such conventional materials may be of natural or synthetic origin and preferably are of a macroporous structure, that is, a structure having a surface area below about 10 m²/g. These support materials typically have an apparent porosity of greater than 20%. Supports having a siliceous and/or aluminous composition are, in general, preferred. Specific examples of suitable supports are the aluminum oxides (including the materials sold under the trade name "Alundum"), pumice, magnesia, zirconia, kieselguhr, fuller's earth, silicon carbide, porous agglomerates comprising silicon and/or silicon carbide, silica, selected clays, artificial and natural zeolites and ceramics. Refractory supports particularly useful in the preparation of the catalysts useful in the process of our invention comprise the aluminous materials, in particular those containing alpha alumina. In the case of alpha alumina-containing supports, preference is given to those having a specific surface area as measured by the B.E.T. method of from about 0.03 to 10 m²/g and an apparent porosity as measured by conventional mercury or water absorption techniques of from about 25 to about 60% by volume. The B.E.T. method for determining specific surface area is described in detail in Brunauer, S., Emmett, P. H., and Teller, E., J. Am. Chem. Soc., 60, 309–16 (1938).

The following materials are specific examples of the catalyst supports which may be used.

I. Norton SN-06595, a fluidizable powder having a surface area of 0.26 m²/g, a total pore volume of 0.675 cc (Hg)/gm, median pore diameter 19 microns (μ), a packing density of 0.98 g/cm³, and a chemical composition (weight percent) of: $Al_2O_3$ - 84.7, $SiO_2$ - 13.4, $Fe_2O_3$ - 0.21, $TiO_2$ - 0.47, CaO - 0.21, MgO - 0.12, $Na_2O$ - 0.15, $K_2O$ - 0.26).

II. Norton SN-08228, 0.1875 inch pellets with a surface area of 0.26 m²/g, a total pore volume of 0.23 cc(Hg)/gm, median pore diameter of 19μ, a packing density of 0.90 g/cm³, and a chemical composition (weight percent) of: alumina - 84.7, $SiO_2$ - 13.4, $Fe_2O_3$ - 0.21, $TiO_2$ - 0.47, CaO - 0.21, MgO - 0.12, $Na_2O$ - 0.15, $K_2O$ - 0.26.

III. Norton SA-5252, 0.1875 inch spheres with a surface area of 0.39 m²/g, a total pore volume of 0.36 cc(Hg)/gm, median pore diameter of 5.4μ, a packing density of 0.94 g/cm³ and a chemical composition (weight percent) as follows: $Al_2O_3$ - 93.1, $SiO_2$ - 5.6, $Fe_2O_3$ - 0.3, $TiO_2$ - 0.1, CaO - 0.1, MgO - 0.3, $Na_2O$ - 0.1, $K_2O$ - 0.1.

IV. Norton 5552 Alumina Rings - 0.25 inch rings having a surface area of 0.43 m²/g, a total pore volume of 0.37 cc (Hg)/gm, a median pore diameter of 7μ, a packing density of 0.80 g/cm³, and a chemical composition (weight percent) of: $Al_2O_3$ - 93.1, $SiO_2$ - 5.6, $Fe_2O_3$ - 0.3, $TiO_2$ - 0.1, CaO - 0.1, MgO - 0.3, $Na_2O$ - 0.1, $K_2O$ - 0.1.

V. Norton SN-82501, 0.1875 inch spheres having a surface area of 0.13 m²/g, a total pore volume of 0.37 cc(Hg)/gm, a median pore diameter of 32.5μ, a packing density of 0.88 g/cm³, and a chemical composition (weight percent) of: $Al_2O_3$ - 85.0, $SiO_2$ - 12.0, and the remaining 3% as $Fe_2O_3$, $TiO_2$, CaO, MgO, $Na_2O$ and $K_2O$.

Although not preferred, other support materials which may be used include zinc oxide, e.g., having a surface area of about 3.9 m²/g and a particle size of about 75–250μ; titania, e.g., having a surface area of about 0.5 m²/g and a particle size of about 40–75μ;

calcium oxide; silica, e.g., having a surface area of about 0.18 m$^2$/g and a particle size of about 75–250μ; barium oxide, e.g., having a surface area of about 1 m$^2$/g and a particle size of 40–75μ; boron nitride; silicon nitride; and silicon carbide.

A preferred class of support materials comprise low surface area, fused, alpha alumina supports which have relatively uniform pore diameters and are more fully characterized by having (1) B.E.T. specific surface areas of from about 0.1 m$^2$/g to about 2.0 m$^2$/g, preferably about 0.3 m$^2$/g, and (2) apparent porosities of from about 42% to about 60%, preferably from about 46% to about 58%.

The actual physical form of the catalyst support is not particularly important. While the form of the catalyst support has little effect on catalyst activity, practical considerations such as ease of heat transfer, mass transfer, pressure drop due to fluid flow restrictions, efficiency of gas-liquid-solid contacting, catalyst durability, and the like make the use of defined shapes such as spheres, pellets, extrudates, rings, saddles, and the like preferred. Conventional commercial fixed-bed reactors used in the epoxidation of ethylenically-unsaturated compounds typically are in the form of a plurality of parallel, or series of, elongated tubes (in a suitable shell). In such reactors, it is desirable to employ a support formed into a rounded shape, such as, for example, spheres, pellets, rings, tablets, and the like, having diameters of from about 0.1 inch to about 0.8 inch.

A preferred method of preparing the catalysts from an inorganic silver compound comprises the steps of (1) forming a catalyst precursor by contacting, in either one or two steps, a porous support material with aqueous solutions of an inorganic silver compound and a modifier compound and drying the resulting impregnated support material, (2) optionally calcining the catalyst precursor wherein a gas such as air, oxygen-depleted air, nitrogen, argon, helium or the like is passed over or through the catalyst precursor at elevated temperatures, and (3) intimately contacting at a temperature of about 170° to 600° C. the catalyst precursor with a gas comprising (i) hydrogen or (ii) an inert gas containing at least 4 volume percent hydrogen. The preparation of the catalysts from an organic silver compound such as a silver amine oxalate, e.g., silver bis-ethylenediamine oxalate, comprises the steps of (1) forming a catalyst precursor by contacting, in either one or two steps, a porous support material with aqueous solutions of an organic silver compound and a modifier compound and drying the resulting impregnated support material, (2) optionally calcining the catalyst precursor wherein a gas such as air, oxygen-depleted air, nitrogen, argon, helium or the like is passed over or through the catalyst precursor at elevated temperatures, and (3) heating the catalyst precursor at a temperature of about 150° to 300° C. to thermally decompose the organic silver compound.

The catalyst precursors may be prepared employing techniques well known to those of skill in the art, such as, for example, by precipitation of suitable silver and modifier compounds on the support, by impregnation, by coprecipitation of the silver and modifier compounds and the support material, by grinding together the support material and the silver and modifier compounds in particulate form and the like. The order in which the modifier is incorporated onto the support material is not critical, e.g., the support may be contacted with a silver source, then the modifier, or the support may be contacted with the modifier compound, then a silver compound, or the support material may be contacted simultaneously with both a modifier compound and a silver compound.

The silver compound employed in the preparation of the catalyst precursor is not critical. Typically, the preparation of the catalyst precursor comprises impregnating the support material with a solution of a silver compound in water, an alcohol, a glycol ether, or a mixture thereof. Exemplary compounds are silver nitrate, silver oxalate, silver acetate, and the like. Those skilled in the art recognize that certain organic silver compounds require the addition of ammonia or an amine in order to solubilize the organic silver compound in an aqueous medium; thus, the use of such solvation-promoting additives is contemplated in the practice of the present invention.

The catalysts may contain about 1 to 30 weight percent silver, calculated as elemental or metallic silver and based on the total weight of active catalyst. The loading level of silver on the support preferably is within the range of about 2 up to 25 weight percent, most preferably about 5 to 20 weight percent, elemental silver. The silver typically is present in the form of uniformly-spaced, discontinuous, adherent, substantially hemispherical, discrete particles having an essentially uniform diameter of about 0.1 to 5.0μ. Catalysts bearing silver particles less than about 0.1μ give inferior catalytic results whereas silver particles larger than about 5.0μ do not appear as uniformly-spaced, discontinuous particles but appear to give a continuous layer of intergrown crystals which results in a catalyst having inferior activity due to loss of silver surface area.

The chemical form of the modifier component of the finished catalysts is not known. However, the heat and/or hydrogen treatment given to the impregnated support in the reduction of the silver salts to metallic silver most likely converts the modifier compounds or salts to an oxide or oxidic compound. The amount of modifier compound present on the catalyst support is expressed herein as the weight percent, based on the total weight of the catalyst, of the modifier element rather than the modifier compound.

The amount of modifier element present on the catalyst surface may vary substantially depending, for example, on the particular support material employed and/or the surface area thereof and the amount of silver on the catalyst. Generally, the amount of modifier element on the active catalyst is in the range of about 10 to 5000 parts per million (ppm, by weight) based on the total weight of the active catalyst. The concentration of modifier preferably is in the range of about 20 to 3000 ppm with amounts in the range of about 50 to 1600 ppm (same basis) being especially preferred. The modifier element preferably is cesium, rubidium or thallium. Normally, the silver:modifier weight ratio of the finished or active catalysts is in the range of about 50:1 to 4000:1, preferably in the range of about 100:1 to 2500:1, and most preferably in the range of about 100:1 to 2000:1.

Silver and the modifier normally are the only active constituents which are added to the support materials in catalytically effective amounts. However, it is not unusual for substantial amounts, often up to about 10,000 ppm by weight of an alkali metal (usually potassium) to be present within the porous support due to (1) the use of support materials containing naturally occurring alkali metals or (2) the addition of alkali metal during support manufacture. These amounts of alkali metal present in the support in non-leachable form, rather than on the surface, do not appear to contribute to the performance of the catalysts.

The catalyst precursor comprising a catalyst support material having the silver and modifier compounds deposited thereon as described hereinabove is converted to an active catalyst by intimately contacting the precursor, after the optional calcination step, with a gas comprising (i) hydrogen, or (ii) an inert gas containing at least about 4 volume percent hydrogen at a temperature of about 170° to 600° C. whereby the silver compound is reduced to elemental silver and the thallium metal compound is believed to be converted to an oxide and/or hydroxide. The particular conditions employed in the high temperature hydrogen treatment can vary substantially since the hydrogen concentration and temperature as well as contact times are interdependent. Alternatively, when the catalyst precursor comprises an organic silver compound, such as an amine-solubilized silver oxalate, the catalyst precursor may be converted to the active state by thermal decomposition in air at temperatures of about 150° to 300° C. Such thermal decomposition requires that the catalyst precursor be heated at a temperature and for a period of time sufficient to completely reduce the organic silver salt to metallic silver.

The olefin reactants which may be used in the process include norbornene, norbornadiene and olefins having the general formula

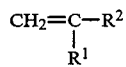

$$CH_2=C-R^2 \quad (I)$$
$$\phantom{CH_2=C-}R^1$$

wherein $R^1$ is hydrogen or alkyl and $R^2$ is an aryl group, a tertiary alkyl group such as tertiary butyl, tertiary amyl, or tertiary octyl, or the group having the formula

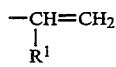

$$-CH=CH_2$$
$$\phantom{-CH=}R^1$$

with the proviso that $R^1$ contains no hydrogen atoms in a position allylic to the ethylenic unsaturation, i.e., the $>C=C<$ group or groups. The alkyl groups represented by $R^1$ may be unsubstituted or substituted alkyl having up to about 12 carbon atoms. Such alkyl groups preferably are unsubstituted alkyl of up to about 4 carbon atoms. When the reactant is an olefin having the formula

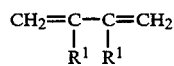

$$CH_2=C-C=CH_2 \quad (I)$$
$$\phantom{CH_2=}R^1\phantom{-}R^1$$

the $R^1$ substituents may be the same or different. The aryl groups represented by $R^2$ may be unsubstituted or substituted carbocyclic aryl having 6 to 10 carbon atoms, e.g., unsubstituted and substituted phenyl and naphthyl radicals. Examples of the substituents which may be present on the aryl groups include alkyl of up to about 4 carbon atoms, alkoxy of up to about 4 carbon atoms, halogen such as chloro and bromo, hydroxy, vinyl, and the like.

The epoxides produced from the olefins of formula (I) in accordance with the epoxidation process described herein have the general formula

wherein $R^1$ and $R^2$ are defined above. The process provided by our invention is especially useful for the selective monoepoxidation of butadiene to 3,4-epoxy-1-butene.

Our novel process may be carried out at a temperature in the range of about 175° to 230° C. with the range of 185° to 225° C. being particularly preferred. The pressure within the epoxidation zone may range from about 0.5 to 20 bars, preferably about 1 to 10 bar. It is apparent that the particular combination of temperature and pressure is selected so as to maintain all of the components of the feed to the epoxidation zone in the gaseous state.

The paraffin hydrocarbons which may be employed as inert diluents in the feed gas to the process of the present invention may be straight- or branched-chain alkanes containing 2 to about 6 carbon atoms, e.g., ethane, propane, butane, isobutane, pentane and hexane. The use of branched-chain hydrocarbons is not preferred due to the reactivity of the tertiary hydrogen atoms of such branched-chain hydrocarbons with the surface chloride atoms on the silver catalyst. Normal butane is the most preferred inert diluent.

The advantages provided by the present invention, i.e., the use of relatively high concentrations of oxygen and increased heat transfer capabilities, may be achieved by feeding to the epoxidation zone a gas comprising about 3 to 30 mole percent of said olefin reactant, about 3 to 30 mole percent oxygen and about 40 to 90 mole percent of the above-described paraffin hydrocarbon containing 2 to 6 carbon atoms, wherein the oxygen:paraffin hydrocarbon mole ratio is in the range of about 0.03:1 to 0.75:1. Normally, the feed gas also will contain a total of about 1 to 10 mole percent of other components such as water, carbon dioxide, argon and recycled epoxide product. Up to about 10 mole percent of the inert diluent component of the feed gas may be made up of one or more other inert gases such as such as argon, methane and nitrogen. The feed gas to our novel continuous process preferably comprises (1) about 5 to 25 mole percent of the olefin reactant, (2) about 5 to 25 mole percent oxygen, (3) about 40 to 80 mole percent of the above-described paraffin hydrocarbon containing 2 to 6 carbon atoms and (4) a total of about 0 to 10 mole percent of other components selected from water, carbon dioxide, argon and recycled epoxide product.

The selectivity of our novel epoxidation process may be increased by performing the process in the presence of halide, typically chloride, ion. Halide ion may be provided to the process by using a halide (chloride) salt of the modifier employed in the preparation of the catalysts. Alternatively, some or all of the halide ion may be provided to the process by including one or more organic halides in the gaseous feed, e.g., in a concentration of about 1 to 40 ppm. Examples of such organic halides include compounds having the formula $R^3X$ wherein $R^3$ is a hydrocarbyl group or a halogenated hydrocarbyl group containing up to about 8 carbon atoms and X is a halogen atom, preferably chloro or bromo, and wherein $R^3$ contains at least one hydrogen atom which is sufficiently acidic so as to render $R^3X$ capable of undergoing dehydrohalogenation under the reaction conditions. Exemplary organic halides include $C_1$ compounds such as methyl chloride, methyl bromide, methylene chloride, methylene bromide, chloroform and bromoform, and the like; $C_2$ compounds such as ethyl chloride, ethyl bromide, dichloroethane, dibromoethane, vinyl chloride, dichloroethylene, trichloroethylene, and the like; $C_3$ compounds such as dichloropropane, dibromopropane, dichloropropene, dibromopropene, and the like; $C_4$ compounds such as chlorobutane, bromobutane, dichlorobutane, dibromo-butane, chlorobutene, bromobutene, dichlorobutene, dibromobutene, and the like; $C_5$ compounds such as mono-, di-, tri-, tetra-, and pentachloropentanes or pentenes, mono-, di-, tri-, tetra-, and pentabromopentanes or pentenes, cyclopentylchloride, cyclopentylbromide, and the like; $C_6$ compounds such as mono-, di-, tri-, tetra-, penta-, and hexachlorohexanes or hexenes, mono-, di-, tri-, tetra-, penta-, and hexabromohexanes or hexenes, cyclohexylchloride, cyclohexylbromide, chlorobenzene, bromobenzene, and the like; $C_7$ compounds such as chlorotoluene, bromotoluene, benzyl chloride, benzyl bromide, mono-, di-, tri-, tetra-, penta--, hexa-, and heptachloroheptanes or heptenes, mono-, di-, tri-, tetra-, penta-, hexa-, and heptabromoheptanes or heptenes, chlorocycloheptane, bromocycloheptane, and the like; $C_8$ compounds such as mono-, di-, tri-, tetra-, penta-, hexa-, hepta- and octachlorooctanes or octenes, mono-, di-, tri-, tetra-, penta-, hexa-, hepta-, and octabromooctanes or octenes, and the like; as well as mixtures of any two or more thereof.

The organic halide can be added to the oxidation reaction zone in a variety of ways. For example, it can be mixed with the olefin to be oxidized and/or the oxygen-containing gas prior to contacting with the catalyst, or the organic halide can be introduced to the reaction zone separately from the feed olefin and/or the oxygen-containing gas. The concentration of the organic halide in the feed to the epoxidation zone preferably is about 2 to 20 parts per million by volume (ppmv). Dichloroethane and chlorobutane are the preferred organic halides.

The novel process of the present invention is further illustrated by the following examples. Unless stated otherwise, the epoxidation catalyst employed in the examples comprised an alumina support in the form of 6 mm outside diameter rings having deposited thereon 12 weight percent silver and 700 parts per million by weight (ppmw) cesium. These catalysts were prepared according to known procedures by impregnating the support material with solutions of a silver amine salt and cesium chloride followed by a thermal decomposition/reduction treatment in the presence of an oxygen-containing gas to convert the silver salt to silver metal.

Two different reactor configurations were used as the epoxidation zones in Examples 1-11 and Comparative Examples 1-6. One configuration (Epoxidation Zone I) consisted of a reactor tube fabricated from Pyrex glass tubing of 30.5 cm length with an inside diameter of 19 mm. A portion of the above described silver/cesium-/alumina catalyst rings was ground and sieved to provide catalyst granules having an irregular shape and a diameter ranging from about 2 to 3.2 mm. The charge (4 g) of these catalyst granules is held in place in the middle portion of the reactor tube by means of a constriction in the reactor diameter. A Chromel/Alumel alloy thermocouple sheathed in stainless steel is embedded within the middle of the catalyst bed to measure reaction temperature. The reactor was heated by means of a tube furnace equipped with a temperature controller. The empty reactor volume above and below the catalyst bed was filled with Pyrex glass beads to ensure that thermal reactions in such empty portions did not occur.

The second reactor configuration (Epoxidation Zone II) consisted of a reactor tube fabricated from Pyrex glass tubing 30.5 cm in length with an expanded section of about 5 cm length and 44.5 mm outside diameter in the middle of the reactor tube. The reactor tubing above and below the expanded region was approximately 12 mm outside diameter. The above described silver/cesium/alumina catalyst rings (25.0 g) were positioned in the expanded section of the reactor tube and the void spaces above and below the catalyst charge were filled with inert glass or ceramic beads to minimize the possibility of thermal, gas phase reactions. Two Chromel/Alumel alloy thermocouples were inserted directly into the catalyst bed, one into the middle of the bed and the other 3 mm from the wall of the reactor. The two thermocouples, spaced 19 mm apart, provided a temperature profile across the width of the catalyst bed. The reactor was heated by means of a tube furnace controlled with a temperature controller.

The results reported in the examples were obtained while operating at steady state conditions using a pressure of 1 bar absolute (1 atmosphere) in a single-pass, flow reactor. The mixture of inert diluent, butadiene and oxygen were fed to the reactor using mass flow controllers in a diluent:butadiene:oxygen molar ratio of 4:1:1 at an overall flow rate of 300 mL (at standard temperature and pressure) per minute. The mass flow controllers provided highly accurate and reproducible flow rates regardless of pressure changes from the supply cylinders or the reactor system downstream from the flow controllers. The 300 mL (STP) per minute rate of feed gas mixture gave a gas hourly space velocity (GHSV, volume of gas fed per hour per volume of catalyst) of 4500 for Epoxidation Zone I and a GHSV of 720 for Epoxidation Zone II. Organic halide (1,2-dichloroethane) was added to the reactor feed gas in a stream of helium containing 100 parts per million by volume (ppmv) 1,2-dichloroethane. Thus, a mass flow controller was set to provide a flow rate that gave organic chloride concentrations of 1 to 20 ppmv in the feed gas.

Analyses of the reaction products and feed compositions were performed using an in-line gas sampling loop connected directly to the inlet of a Varian 3760 gas chromatograph. Both thermal conductivity (TC) and flame ionization (FI) detectors [(connected in series below the packed Chromosorb 101 column (8 ft. by 2 mm id Pyrex glass capillary column)] were used to analyze all of the reaction products. The TC detector gave quantitative analyses for oxygen, carbon dioxide, water and formaldehyde (if present), while the FI detector is used for organic molecules such as butadiene, butadiene monoxide, crotonaldehyde, 2,5-dihydrofuran, furan and acrolein. In practice, however, usually only the selective epoxidation product and olefin feedstock are present as organic molecules. Further, by means of a switching valve, it is possible to divert the feed stream through the in-line sample loop prior to passage over the catalyst. In this way, quantitative analysis of the feed stream and comparison to the corresponding data from the reactor effluent are possible, thereby providing very accurate measurements of both conversion levels and product selectivities. Output from both the TC and FI detectors are integrated using computing integrators which are programmed to give both absolute quantities and rates of formation. All reactor exit lines are heated and maintained at 125°–140° C. to prevent product condensation.

The GC analysis is performed using the following temperature programming schedule: an initial temperature of 100° C. is held for 5 minutes, followed by a temperature program rate of +10° C./minute up to a final temperature of 200° C. which is then held for 7 minutes.

As used herein, conversion is the mole percent conversion of butadiene defined as:

$$\frac{\text{Moles butadiene converted to products}}{\text{Moles butadiene fed}} \times 100$$

and selectivity is the percent selectivity to 3,4-epoxy-1-butene defined as:

$$\frac{\text{Moles butadiene converted to 3,4-epoxy-1-butene}}{\text{Moles butadiene converted to total products}} \times 100$$

The heat capacity ($C_p$) expressed in units of calorie per degree-mole at 200° C. for each of the inert diluent gases used in the examples is:

Helium = 4.97   Methane = 10.75   Ethane = 17.91
Propane = 25.86   Normal Butane = 34.16

EXAMPLES 1–3 AND COMPARATIVE EXAMPLES 1 AND 2

The reactor constituting Epoxidation Zone I was heated to 160° C. in flowing inert diluent gas prior to the addition of the butadiene, oxygen, and, typically, 2–3 ppmv of 1,2-dichloroethane (DCE) to the inert gas to complete the composition of the reactant feed gas. The level of DCE was increased incrementally to maintain the desired selectivity values as well as optimize the thermal control of the reaction at the desired level of butadiene conversion. The concentration of DCE in the feed gas of each of the examples was 5 ppmv. The target value of approximately 12 mole percent butadiene conversion in the reactor was reached by increasing the reaction temperature until this level of butadiene conversion was attained. The inert diluent gases used in these examples were:

Comparative Example 1 (C-1) - Helium
Comparative Example 2 (C-2) - Methane
Example 1 - Ethane   Example 2 - Propane
Example 3 - n-Butane The results obtained are shown in Table I wherein $C_p$ is the cumulative heat capacity of the gas mixture fed to the reactor, TEMP is the temperature in °C. detected by the catalyst bed thermocouple, CONV and SELECT are conversion and selectivity, respectively, as defined above, and TOTAL HEAT OF REACTION expressed as calorie per minute for EpB and water/carbon dioxide determined as follows: for EpB—fractional conversion of butadiene × fractional selectivity to EpB×0.0022 moles butadiene per minute ×23.6 kilocalories/mole EpB formed; for water/carbon dioxide—fractional conversion ×(1.0 - fractional selectivity to EpB)×0.0022 moles butadiene per minute ×552.3 kilocalories/mole EpB combusted.

TABLE I

| Example | $C_p$ of Feed Gas | TEMP | CONV | SELECT | TOTAL HEAT OF REACTION |
|---|---|---|---|---|---|
| C-1 | 9.22 | 225 | 12.8 | 93.8 | 16.10 |
| C-2 | 13.07 | 220 | 12.4 | 95.1 | 13.90 |
| 1 | 18.30 | 202 | 12.0 | 93.7 | 15.23 |
| 2 | 23.14 | 189 | 12.8 | 94.0 | 15.76 |
| 3 | 28.68 | 179 | 12.8 | 93.8 | 16.07 |

The data presented in Table I show that for similar levels of conversion and selectivity, the higher heat capacities of ethane, propane and n-butane result in an overall lower reaction temperature to achieve similar yields of EpB. The benefits of operating at lower temperatures have been mentioned earlier. In addition, lower operating temperatures would be expected to give longer catalyst lifetimes, lower the rates of nonselective thermal reactions between butadiene and oxygen, and lower costs for reactor operation.

EXAMPLES 4 AND 5

The maximum temperature of operability, i.e., before uncontrollable exothermic behavior was encountered, for n-butane and for a mixture of propane and helium in a 1:1 mole ratio (having a cumulative $C_p$ of 15.42) was determined using the procedure employed in the preceding examples. In Example 4, the feed gas was composed of helium:propane:butadiene:oxygen in a mole ratio of 2:2:1:1 whereas the feed gas in Example 5 was composed of n-butane:butadiene:oxygen in a mole ratio of 4:1:1. The feed gas used in each example contained 5 ppmv DCE. The results obtained are shown in Table II wherein the terms used have the meanings given to them above.

TABLE II

| Example | $C_p$ of Feed Gas | TEMP | CONV | SELECT | TOTAL HEAT OF REACTION |
|---|---|---|---|---|---|
| 4 | 16.18 | 214 | 16.7 | 92.1 | 24.3 |
| 5 | 28.68 | 210 | 20.5 | 90.1 | 34.7 |

These examples demonstrate that the higher heat capacities of the feed gas when using butane or propane as the inert diluent permit higher levels of butadiene conversion in the reactor while still retaining thermal stability. The total heat of reaction for Example 5 (34.7 calories/minute) is more than twice that for Example C-1 in which the inert diluent is helium. The data for Example C-1 in Table I represent the highest level of butadiene conversion that can be attained for helium before thermal instability occurs, i.e., before the occurrence of an exothermic temperature excursion. The data presented in Table II thus show that the higher heat capacities of the hydrocarbon diluents, n-butane and propane, are able to provide a superior heat sink for the extra heat of reactions generated for the increased yields of EpB.

EXAMPLES 6–8 AND COMPARATIVE EXAMPLES 3 AND 4

Examples 1–3 and Comparative 1 and 2 were repeated using the reactor constituting Epoxidation Zone II. These data are identified as Examples 6–8 and Comparative Examples 3 and 4, respectively, Four ppmv DCE were used in the feeds in Comparative Example 3 and Example 6 and 3 ppmv DCE were used in the feeds in Comparative Example 4 and Examples 7 and 8. The reactor was heated to 160° C. in flowing inert diluent gas prior to the addition of the butadiene, oxygen and DCE to the inert gas to complete the composition of the reactant feed gas. The DCE concentration was increased incrementally to maintain the desired selectivity as well as optimize the thermal stability at the target value of approximately 12 mole percent butadiene conversion. The inert diluent gases used in these examples were:

| Comparative Example 3 (C-3) - Helium |
| Comparative Example 4 (C-4) - Methane |
| Example 6 - Ethane    Example 7 - Propane |
| Example 8 - n-Butane |

The results obtained are shown in Table III wherein the terms used have the meanings given to them above and TEMPERATURE, Mid and TEMPERATURE, Out are the temperatures (° C.) at the middle and outside of the catalyst bed, respectively.

TABLE III

| Ex-ample | TEMPERATURE Mid | Out | CONV | SE-LECT | TOTAL HEAT OF REACTION |
|---|---|---|---|---|---|
| C-3 | 220 | 218 | 12.2 | 93.1 | 15.8 |
| C-4 | 211 | 211 | 12.4 | 94.8 | 13.6 |
| 6 | 208 | 209 | 12.1 | 94.2 | 14.3 |
| 7 | 198 | 200 | 12.7 | 93.6 | 15.2 |
| 8 | 190 | 192 | 12.6 | 92.7 | 16.4 |

The data set forth in Table III further establish that for similar levels of conversion and selectivity the higher heat capacities of ethane, propane and n-butane diluents result in an overall lower reaction temperature to achieve similar production rates of EpB. The relatively constant temperature profile across the catalyst bed shows that the diluent gases distribute the heat of reaction evenly across the catalyst bed.

EXAMPLES 9–11 AND COMPARATIVE EXAMPLES 5 AND 6

Examples 6–8 and Comparative Examples 3 and 4 were repeated using the apparatus constituting Epoxidation Zone II except that reaction temperatures were increased to determine the maximum temperature of stable operation before uncontrollable temperature exotherms were encountered. The overall yields for EpB at these conditions were calculated. Since selectivity values were relatively constant in all cases, the yields for EpB are directly proportional to the percent conversion of butadiene. The concentration of DCE in the feeds in Comparative Examples 5 and 6 and Example 10 was 5 ppmv and in the feeds for Examples 9 and 11 it was 6 ppmv. The inert diluent gases used in these examples were:

| Comparative Example 5 (C-5) - Helium |
| Comparative Example 6 (C-6) - Methane |
| Example 9 - Ethane    Example 10 - Propane |
| Example 11 - n-Butane |

The results obtained are shown in Table IV wherein the terms used have the meanings given to them above and TEMPERATURE, Mid and TEMPERATURE, Out are the temperatures (°C.) at the middle and outside of the catalyst bed, respectively.

TABLE IV

| Ex-ample | $C_p$ of Feed Gas | TEM-PERATURE Mid | Out | CONV | SELECT | TOTAL HEAT OF REACTION |
|---|---|---|---|---|---|---|
| C-5 | 9.22 | 225.8 | 223.3 | 14.3 | 92.5 | 20.6 |
| C-6 | 13.07 | 221 | 220 | 14.0 | 93.4 | 17.8 |
| 9 | 18.30 | 225.8 | 225 | 16.6 | 91.1 | 25.8 |
| 10 | 23.14 | 220.7 | 222.8 | 19.1 | 89.5 | 33.5 |
| 11 | 28.68 | 218.7 | 217.2 | 19.9 | 89.4 | 34.9 |

The data presented in Table IV show that the higher heat capacities of the ethane, propane and n-butane diluents provide a superior heat sink for the heat of reaction in the epoxidation of butadiene to EpB. The higher heat capacities permit operation of the epoxidation process at higher butadiene conversion levels which provides for the production of greater amounts of EpB using the same production apparatus and the same amount of catalyst.

EXAMPLES 12 AND 13 AND COMPARATIVE EXAMPLES 7 AND 8

These examples were performed in a bench-scale, continuous, epoxidation apparatus in which materials are recycled to the epoxidation zone analogous to the production system depicted in the process flow diagram of U.S. Pat. No. 5,117,012. The catalyst employed in Examples 12 and 13 and Comparative Examples 7 and 8 was the silver/cesium/alumina catalyst rings described hereinabove. The epoxidation zone comprised a staged, adiabatic reactor which consisted of 3 sections of stainless steel pipe having an outside diameter of approximately 4 cm provided with forced air cooling between stages 1 and 2 and stages 2 and 3. The stages were charged with the following lengths of catalyst:

Stage 1—26.7 cm
Stage 2—35.6 cm
Stage 3—44.5 cm

The total volume of catalyst charged was 1.5 liters. Thermocouples were placed at the start of each catalyst bed and then at 9 cm intervals over the length of the bed. The last thermocouple for each bed was at the end of the catalyst in order to obtain a $\Delta T$ for each stage. Isothermal conditions were simulated by placing a 5.1 cm layer of insulating mat around each stage followed by a 5.1 cm wide heating tape and then another 2.5 cm of insulating mat. The voltage applied to the heating tape was controlled by means of a rheostat. Just prior to the start of the oxygen feed to the reactor, the voltage setting was adjusted as necessary to give for each stage an inlet and outlet temperature of about 210° C.

The average composition (in mole percentages) of the feeds used in each of the examples and the amount (in ppmv) of the 1,2-dichloroethane (DCE) or 2-chlorobutane (2-CB) in the feed were:

| Example 12: | Butane - 71% | Argon - 10% |
| | Oxygen - 12% | Butadiene - 7 |
| | DCE - 3.1 | |
| Example 13: | Butane - 70% | Argon - 10% |
| | Oxygen - 12% | Butadiene - 8 |
| | 2-CB - 7 | |
| Comparative Example 7: | Nitrogen - 62% | Argon - 9% |
| | Oxygen - 8% | Butadiene - 21 |
| | DCE - 5 | |
| Comparative Example 8: | Methane - 64% | Argon - 9% |
| | Oxygen - 8% | Butadiene - 19 |

DCE - 6

No attempt was made to maintain constant butadiene concentrations in the inlet feed since under these conditions the reaction rates and selectivities were independent of butadiene concentration. The overall feed rate to the epoxidation zone in each example was 175 standard liters per minute.

The ΔT of the reactor was controlled by adjusting the inlet temperature to each reactor stage, the concentration of the halide modifier in the feed, the oxygen concentration in the feed, or a combination thereof. Usually the oxygen and halide modifier feed concentrations are fixed and the reactor is controlled by adjusting the inlet temperatures to maintain the desired ΔT for each stage.

The effluent of each reactor stage was analyzed on a HP Model 5890 Gas Chromatograph using a 25M×0.32 mm Poraplot Q (Chrompak) column connected to a micro TC detector. Samples were taken via a series of 6-port sampling/switching valves with a 0.419 cc sample loop. The gas sampling/switching valves were heated at 130° C. The typical pressure of the sample loop was 1.04 bar absolute. The TC detector was calibrated prior to start up to obtain relative response factors for all the components.

The results obtained are shown in Table V wherein $C_p$ of Feed Gas, CONV, SELECT and TOTAL HEAT OF REACTION are defined above, INLET TEMP is given for the temperature (°C.) of the feed gas at the front of the catalyst bed located in of each of the three reactor stages (St1, St2 and St3), and ΔT is the temperature (°C.) differential between the front and back ends of the catalyst bed located in each of the three reactor stages (ST1, St2 and St3). The Total ΔT is the sum of the temperature (°C.) differentials over each of the three stages. The results set forth in Table V below are the averages obtained for a 24 hour period during steady state operation of each run which typically involved between 2 to 12 weeks of continuous operation.

The space-time yield (STY) or production rate set forth in Table V for each example is expressed as grams 3,4-epoxy-1-butene produced per liter catalyst-hour. The STY values given for the three reactor stages are cumulative, e.g., the STY given for St2 is the total for Stages 1 and 2.

TABLE V

| | Example C-7 | Example C-8 | Example 12 | Example 13 |
|---|---|---|---|---|
| Cp of Feed Gas | 11.30 | 13.25 | 27.59 | 27.53 |
| INLET TEMP. | | | | |
| St1 | 207.1 | 201.1 | 196.2 | 197.5 |
| St2 | 208.5 | 206.4 | 198.5 | 199.3 |
| St3 | 213.0 | 216.5 | 200.4 | 198.8 |
| ΔT | | | | |
| St1 | 17.9 | 20.4 | 11.3 | 11.2 |
| St2 | 18.4 | 12.9 | 11.2 | 11.0 |
| St3 | 13.8 | 9.0 | 11.5 | 10.4 |
| Total | 50.1 | 42.3 | 34.0 | 32.6 |
| CONV. | | | | |
| St1 | 1.82 | 2.45 | 6.13 | 5.37 |
| St2 | 3.97 | 5.20 | 11.30 | 10.67 |
| St3 | 5.48 | 6.38 | 15.74 | 15.27 |
| SELECT | 90 | 94 | 92 | 92 |
| TOTAL HEAT OF REACTION | | | | |
| St1 | 2.29 | 2.01 | 2.30 | 2.13 |

TABLE V-continued

| | Example C-7 | Example C-8 | Example 12 | Example 13 |
|---|---|---|---|---|
| St2 | 4.98 | 4.27 | 4.25 | 4.23 |
| St3 | 6.87 | 5.24 | 5.91 | 6.05 |
| STY | | | | |
| St1 | 291.6 | 373.3 | 366.9 | 330.0 |
| St2 | 275.5 | 338.0 | 291.6 | 275.5 |
| St3 | 232.3 | 248.3 | 240.3 | 237.1 |

The data presented in Table V show that for similar production rates (at substantially the same selectivities), the higher heat capacities provided by the use of butane result in both overall lower ΔT's through the reactor and lower reactor temperatures. In addition to the benefits previously mentioned, the lower ΔT's obtained with butane as the diluent provide a wider range of safe operability of the reactor.

EXAMPLE 14 AND COMPARATIVE EXAMPLE 9

These example were carried out using the procedure and apparatus described in Examples 12 and 13 and Comparative Examples 7 and 8. The catalyst employed was the silver/cesium/alumina catalyst rings described hereinabove. The total volume of catalyst charged was 1.5 liters. The average composition (in mole percentages) of the feeds used in the examples and the amount (in ppmv) of the 1,2-dichloroethane (DCE) or 2-chlorobutane (2-CB) in the feed were:

| Example 14: | Butane - 71% | Argon - 9% |
| | Oxygen - 12% | Butadiene - 8 |
| | 2-CB - 7 | |
| Comparative Example 9: | Methane - 64% | Argon - 8% |
| | Oxygen - 12% | Butadiene - 16 |
| | DCE - 1.5 | |

The overall feed rate to the epoxidation zone in each example was 175 standard liters per minute.

The results obtained are set forth in Table VI wherein the various terms and abbreviations have the meanings given for Table V.

TABLE VI

| | Example C-9 | Example 14 |
|---|---|---|
| Cp of Feed Gas | 12.65 | 27.83 |
| INLET TEMP. | | |
| St1 | 187.2 | 205.6 |
| St2 | 199.3 | 203.7 |
| St3 | 202.8 | 200.0 |
| ΔT | | |
| St1 | 21.4 | 13.0 |
| St2 | 12.9 | 16.8 |
| St3 | 10.8 | 16.8 |
| Total | 45.1 | 46.6 |
| CONV. | | |
| St1 | 3.24 | 6.73 |
| St2 | 5.34 | 15.63 |
| St3 | 7.34 | 21.75 |
| SELECT | 95 | 90 |
| TOTAL HEAT OF REACTION | | |
| St1 | 2.03 | 3.15 |
| St2 | 3.34 | 7.32 |
| St3 | 4.59 | 10.19 |
| STY | | |
| St1 | 428.4 | 397.3 |
| St2 | 302.3 | 387.7 |

TABLE VI-continued

| | Example C-9 | Example 14 |
|---|---|---|
| St3 | 237.6 | 322.0 |

The results reported in Table VI clearly establish that the higher heat capacity of butane allows substantially higher production rates to be achieved under similar reactor temperature increases.

The invention has been described in detail with particular reference to preferred embodiments thereof, but it will be understood that variations and modifications may be effected within the spirit and scope of the invention.

We claim:

1. A continuous process for the preparation of the monoepoxide of an olefin reactant selected from norbornene, norbornadiene and olefins having the general formula

wherein $R^1$ is hydrogen or alkyl and $R^2$ is an aryl radical or the group

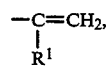

provided that the olefins of formula (I) do not contain any allylic hydrogen atoms, which comprises the steps of:
   (1) continuously feeding a gas comprising about 3 to 30 mole percent of said olefin reactant, about 3 to 30 mole percent oxygen and about 40 to 90 mole percent of a paraffin hydrocarbon containing 2 to 6 carbon atoms wherein the oxygen:paraffin hydrocarbon mole ratio is in the range of about 0.03:1 to 0.75:1 to an epoxidation zone containing a supported, silver epoxidation catalyst and maintained at a temperature of about 175° to 230° C.; and
   (2) continuously removing from the epoxidation zone a gas comprising about 0.5 to 3.5 mole percent of said monoepoxide of the olefin reactant, about 2 to 28 mole percent of said olefin reactant, about 2 to 28 mole percent oxygen and about 40 to 90 mole percent of said paraffin hydrocarbon.

2. Process according to claim 1 wherein the epoxidation catalyst comprises a catalyst support material having deposited on its surface about 1 to 30 weight percent silver and about 10 to 5000 parts per million by weight (ppmw) of an epoxidation catalyst modifier selected from alkali earth metals, alkaline earth metals and thallium.

3. Process according to claim 2 wherein the olefin reactant is 1,3-butadiene and the monoepoxide is 3,4-epoxy-1-butene.

4. A continuous process for the preparation of 3,4-epoxy-1-butene which comprises the steps of:
   (1) continuously feeding a gas comprising about 5 to 25 mole percent of 1,3-butadiene, about 5 to 25 mole percent oxygen and about 40 to 80 mole percent of a paraffin hydrocarbon containing 2 to 6 carbon atoms wherein the oxygen:paraffin hydrocarbon mole ratio is in the range of about 0.03:1 to 0.75:1 to an epoxidation zone containing a supported, silver epoxidation catalyst and maintained at a temperature of about 175° to 230° C.; and
   (2) continuously removing from the epoxidation zone a gas comprising about 0.5 to 3.5 mole percent of said monoepoxide of the olefin reactant, about 2 to 28 mole percent of said olefin reactant, about 2 to 28 mole percent oxygen and about 40 to 90 mole percent of said paraffin hydrocarbon.

5. Process according to claim 4 wherein the epoxidation catalyst comprises a catalyst support material having deposited on its surface about 2 to 25 weight percent silver and about 20 to 3000 parts per million by weight (ppmw) of an epoxidation catalyst modifier selected from alkali earth metals, alkaline earth metals and thallium.

6. A continuous process for the preparation of 3,4-epoxy-1-butene which comprises the steps of:
   (1) continuously feeding a gas comprising about 5 to 25 mole percent of 1,3-butadiene, about 5 to 25 mole percent oxygen and about 40 to 80 mole percent butane wherein the oxygen:butane mole ratio is in the range of about 0.03:1 to 0.75:1 to an epoxidation zone containing a supported, silver epoxidation catalyst comprising a catalyst support material having deposited on its surface about 2 to 25 weight percent silver and about 20 to 3000 parts per million by weight (ppmw) of an epoxidation catalyst modifier selected from cesium and rubidium and maintained at a temperature of about 175° to 230° C.; and
   (2) continuously removing from the epoxidation zone a gas comprising about 0.5 to 3.5 mole percent of said monoepoxide of the olefin reactant, about 2 to 28 mole percent of said olefin reactant, about 2 to 28 mole percent oxygen and about 40 to 90 mole percent butane.

* * * * *